(12) United States Patent
Carper (10) Patent No.: US 12,083,465 B2
(45) Date of Patent: Sep. 10, 2024

(54) SYSTEMS AND METHODS FOR ANTI-MICROBIAL PURIFICATION OF AIR

(71) Applicant: The Boeing Company, Chicago, IL (US)

(72) Inventor: Judd Steven Carper, Colorado Springs, CO (US)

(73) Assignee: The Boeing Company, Arlington, VA (US)

( * ) Notice: Subject to any disclaimer, the term of this patent is extended or adjusted under 35 U.S.C. 154(b) by 386 days.

(21) Appl. No.: 16/694,493

(22) Filed: Nov. 25, 2019

(65) Prior Publication Data

US 2021/0154609 A1 May 27, 2021

(51) Int. Cl.
| | | |
|---|---|---|
| *B01D 46/00* | (2022.01) | |
| *A61L 9/16* | (2006.01) | |
| *B01D 46/62* | (2022.01) | |
| *B01D 46/66* | (2022.01) | |
| *B64D 13/06* | (2006.01) | |
| *C12N 1/06* | (2006.01) | |
| *C12N 13/00* | (2006.01) | |

(52) U.S. Cl.
CPC ............ *B01D 46/0028* (2013.01); *A61L 9/16* (2013.01); *B01D 46/62* (2022.01); *B01D 46/785* (2022.01); *B64D 13/06* (2013.01); *C12N 1/066* (2013.01); *C12N 13/00* (2013.01); *A61L 2209/14* (2013.01); *B01D 2239/0442* (2013.01); *B01D 2239/0478* (2013.01); *B64D 2013/0651* (2013.01)

(58) Field of Classification Search
CPC .. B01D 46/0028; B01D 46/62; B01D 46/785; B01D 2239/0442; B01D 2239/0478; A61L 9/16; A61L 2209/14; B64D 13/06; B64D 2013/0651; C12N 1/066; C12N 13/00

USPC ................... 96/223–227, 15–100; 95/15–100
See application file for complete search history.

(56) References Cited

U.S. PATENT DOCUMENTS

| 5,433,772 A | * | 7/1995 | Sikora | ........................ B03C 3/32 |
| | | | | 55/357 |
| 5,466,279 A | * | 11/1995 | Hattori | ...................... B03C 3/47 |
| | | | | 96/100 |
| 5,564,626 A | * | 10/1996 | Kettler | ...................... F24F 8/10 |
| | | | | 55/471 |

(Continued)

FOREIGN PATENT DOCUMENTS

| CN | 108673970 A | 10/2018 |
| CN | 112010292 A | 12/2020 |

(Continued)

OTHER PUBLICATIONS

European Extended Search Report regarding European Patent Application No. 20207566.9 dated May 7, 2021; pp. 1-7.

(Continued)

*Primary Examiner* — T. Bennett McKenzie
(74) *Attorney, Agent, or Firm* — Alleman Hall & Tuttle LLP (57) ABSTRACT

An air supply system including a conduit for channeling a flow of air therethrough, wherein the flow of air has microorganisms entrained therein. The system also includes an anti-microbial filter in flow communication with the flow of air. The anti-microbial filter includes a plurality of atomically sharp surface features for non-selective lysing of at least some of the microorganisms that contact the anti-microbial filter.

20 Claims, 5 Drawing Sheets

(56) References Cited

U.S. PATENT DOCUMENTS

| | | | | |
|---|---|---|---|---|
| 5,938,823 | A * | 8/1999 | Condit | B03C 3/017 |
| | | | | 96/225 |
| 7,001,447 | B1 * | 2/2006 | Altman | B03C 3/74 |
| | | | | 323/903 |
| 8,628,953 | B2 | 1/2014 | Osato et al. | |
| 2002/0139251 | A1 * | 10/2002 | Simmons | B60H 1/34 |
| | | | | 55/385.3 |
| 2010/0050872 | A1 * | 3/2010 | Lee | B01D 46/546 |
| | | | | 977/777 |
| 2010/0282083 | A1 | 11/2010 | Edwards | |
| 2012/0130099 | A1 | 5/2012 | Wittenberg et al. | |
| 2013/0068106 | A1 * | 3/2013 | Hartmann | B01D 46/0086 |
| | | | | 96/417 |
| 2013/0291736 | A1 * | 11/2013 | Jung | B01D 46/0028 |
| | | | | 156/379.7 |
| 2015/0107449 | A1 * | 4/2015 | Son | A47L 9/19 |
| | | | | 95/2 |
| 2015/0184224 | A1 | 7/2015 | Guy et al. | |
| 2016/0212989 | A1 * | 7/2016 | Juodkazis | A01N 25/34 |
| 2016/0236131 | A1 * | 8/2016 | Lin | G03B 21/16 |
| 2017/0007953 | A1 * | 1/2017 | Lee | F24F 1/0073 |
| 2017/0137610 | A1 * | 5/2017 | You | C08K 9/02 |
| 2019/0063763 | A1 * | 2/2019 | Kleinberger | A61L 2/022 |

FOREIGN PATENT DOCUMENTS

| | | |
|---|---|---|
| CN | 212511668 U | 2/2021 |
| EP | 3994296 | 5/2022 |
| WO | 2018033793 A1 | 2/2018 |

OTHER PUBLICATIONS

European Patent Office, Extended European Search Report Issued in Application No. 23203831.5, Feb. 14, 2024, Germany, 5 pages.
European Patent Office, Extended European Search Report Issued in Application No. 24157450.8, May 23, 2024, 5 pages.

* cited by examiner

SYSTEMS AND METHODS FOR ANTI-MICROBIAL PURIFICATION OF AIR

FIELD

The field relates generally to air supply systems and, more specifically, to an anti-microbial air supply system that purifies air by lysing microorganisms entrained in the air supply.

BACKGROUND

Antibiotic and anti-microbial resistant bacteria and viruses are sometimes referred to as "superbugs." At least some known superbugs are derived from preferential selectivity of microorganisms in a strain as a result of exposure to an antibiotic or anti-microbial agent, for example. The preferential selectivity is based on the resistance of the microorganisms to the antibiotic or anti-microbial agent. For example, the antibiotic or anti-microbial agent may be effective at killing or inhibiting the growth of weaker microorganisms in the strain, but may be ineffective in regards to stronger microorganisms in the strain. Survival of the stronger microorganisms enables the creation of superbugs that are increasingly resistant to antibiotics, anti-microbial agents, and other forms of wet chemistry. The proliferation and prevalence of superbugs is an important health issue that is taken into consideration in the design of air supply systems that provide and recirculate air within confined spaces designed for human occupancy, such as confined spaces of vehicles. At least some known air supply systems use anti-microbial filter media designed to collect microorganisms before they can be provided to the confined spaces. However, the filter media has a limited service life, which may increase the cost and complexity of the air supply system.

This section is intended to introduce the reader to various aspects of art that may be related to various aspects of the disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

BRIEF DESCRIPTION

One aspect is an air supply system for channeling a flow of air wherein the flow of air has entrained microorganisms. The system also includes an anti-microbial filter in communication with the flow of air. The anti-microbial filter includes atomically sharp surface features for non-selective lysing of at least some of the entrained microorganisms.

In another aspect, an aircraft includes a confined space, and an air supply system for providing a flow of purified air to the confined space. The air supply system includes a conduit for channeling a flow of air, wherein the flow of air has microorganisms entrained therein. The system also includes an anti-microbial filter in communication with the flow of air. The anti-microbial filter includes a plurality of atomically sharp surface features for non-selectively lysing at least some of the microorganisms that contact the anti-microbial filter.

In yet another aspect, a method of purifying air includes channeling a flow of air, having microorganisms entrained therein, towards an anti-microbial filter. The anti-microbial filter includes a plurality of atomically sharp surface features. The method also includes controlling a velocity of the flow of air, wherein the velocity is selected to facilitate non-selective lysing of at least some of the microorganisms that contact the anti-microbial filter, and discharging a flow of purified air from the anti-microbial filter.

Various refinements exist of the features noted in relation to the above-mentioned aspects of the present disclosure. Further features may also be incorporated in the above-mentioned aspects of the present disclosure as well. These refinements and additional features may exist individually or in any combination. For instance, various features discussed below in relation to any of the illustrated embodiments of the present disclosure may be incorporated into any of the above-described aspects of the present disclosure, alone or in any combination.

BRIEF DESCRIPTION OF THE DRAWINGS

FIG. 1 is a cross-sectional illustration of an example aircraft fuselage.

FIG. 2 is a schematic illustration of an example air supply system that may be used with the aircraft fuselage shown in FIG. 1.

FIG. 3 is a partial view illustration of an example anti-microbial filter that may be used in the air supply system shown in FIG. 2.

FIG. 4 is a partial view illustration of an alternative anti-microbial filter that may be used in the air supply system shown in FIG. 2.

FIG. 5 is a block diagram illustrating the air supply system shown in FIG. 2.

Corresponding reference characters indicate corresponding parts throughout the drawings.

DETAILED DESCRIPTION

The implementations described relate to an anti-microbial air supply system that purifies air by lysing microorganisms, such as viruses, bacteria, fungi, and protists, entrained therein. The air supply system includes an anti-microbial filter positioned to be in flow communication with a flow of air, having the microorganisms entrained therein, channeled through a conduit. The anti-microbial filter includes a filtration surface having a plurality of atomically sharp surface features defined thereon. The atomically sharp surface features facilitate forming a micro-machined spike field designed to mechanically damage (i.e., lyse) microorganisms that come into contact with the atomically sharp surface features, thereby destroying the microorganisms regardless of their resistance to antibiotics, anti-microbial agents, or other forms of wet chemistry (i.e., non-selectivity). Accordingly, the systems and methods described herein facilitate reducing the propagation of microbial life and improving air quality without contributing to the formation of superbugs as a result of preferential selectivity (i.e., the antithesis of non-selectivity).

As used herein, an element or step recited in the singular and preceded with the word "a" or "an" should be understood as not excluding plural elements or steps, unless such exclusion is explicitly recited. Furthermore, references to "example implementation" or "one implementation" of the present disclosure are not intended to be interpreted as excluding the existence of additional implementations that also incorporate the recited features.

As used herein, the term "aircraft" may include, but is not limited to only including, airplanes, unmanned aerial vehicles (UAVs), gliders, helicopters, manned spacecraft, and/or any other object that travels through airspace. Further, in an alternative implementation, the systems and methods described herein may be used with any vehicle or confined space designed for human occupancy.

Figure 1:
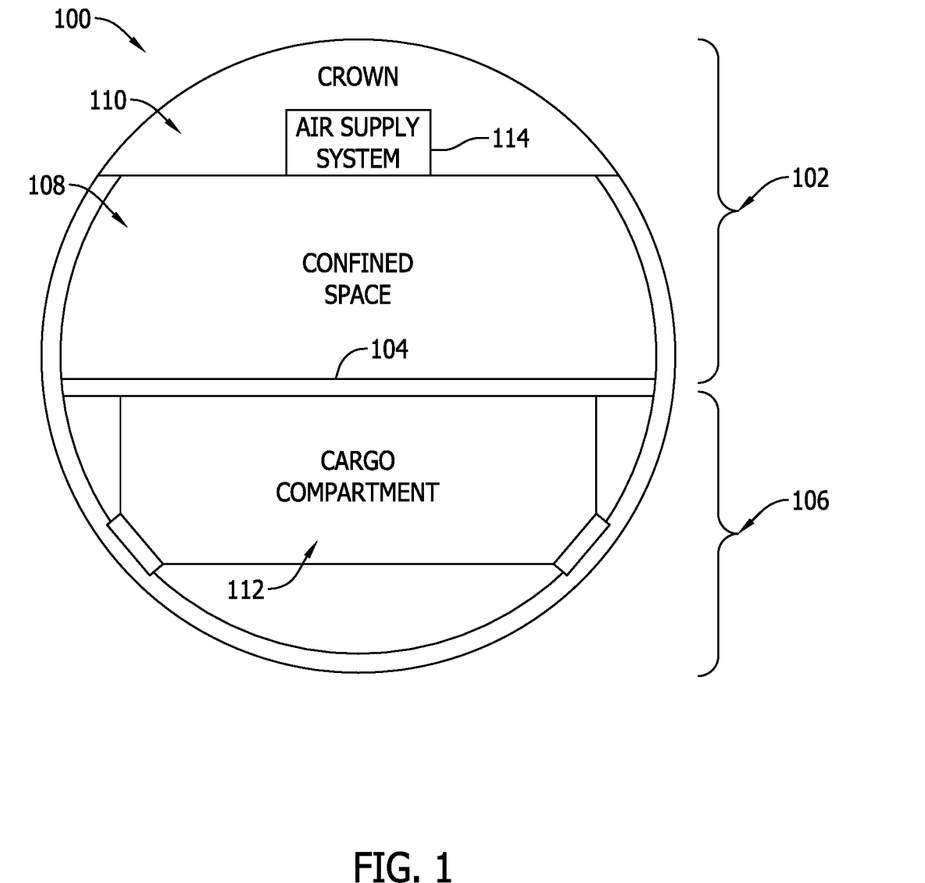

FIG. 1 is a cross-sectional illustration of an example aircraft fuselage 100. In the example implementation, aircraft fuselage 100 includes an upper lobe 102 located above a floor beam 104, and a lower lobe 106 located below floor beam 104. Upper lobe 102 includes a confined space 108 and a crown 110, and lower lobe 106 includes a cargo compartment 112. An air supply system 114 is positioned within crown 110, and is operable to provide a flow of purified air to confined space 108. Although air supply system 114 is depicted as being positioned within crown 110, one or more components of air supply system 114 may be positioned within other areas of upper lobe 102 or lower lobe 106.

Figure 2:
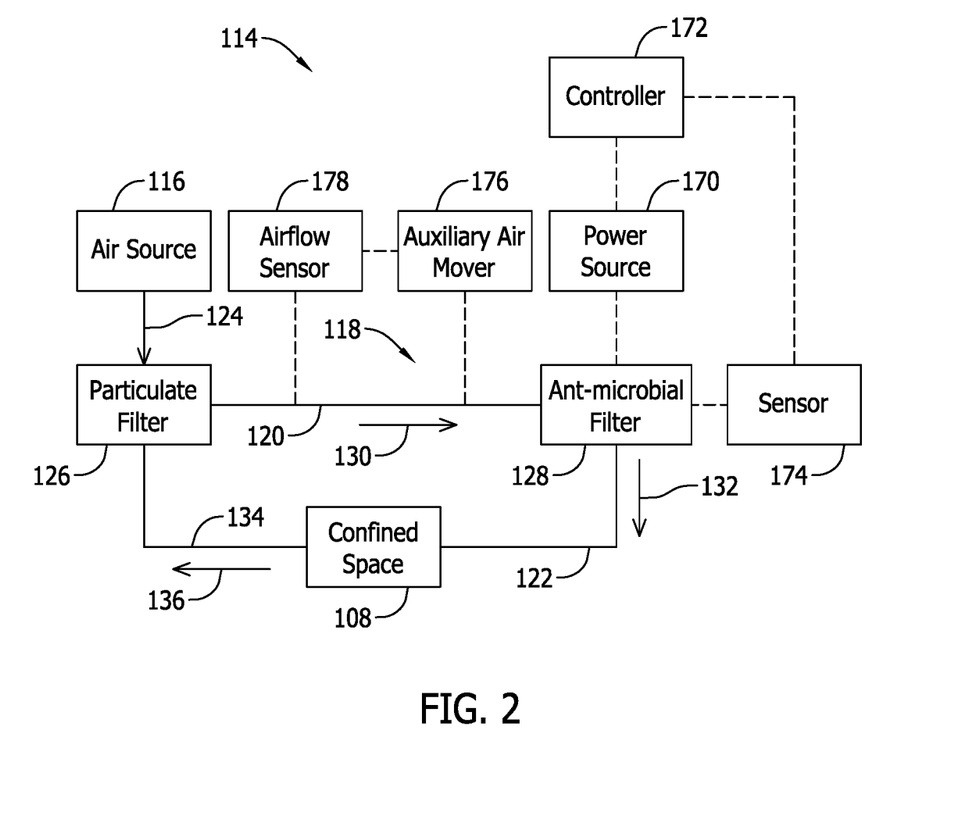

FIG. 2 is a schematic illustration of air supply system 114 that may be used with aircraft fuselage 100 (shown in FIG. 1). In the example implementation, air supply system 114 includes an air source 116 in flow communication with confined space 108 via a conduit 118 that includes a first conduit section 120 and a second conduit section 122. Air source 116 may be any source of air that enables air supply system 114 to function as described herein. For example, air source 116 may provide confined space 108 with a flow of ambient air 124.

Air supply system 114 also includes a particulate filter 126 and an anti-microbial filter 128, which are in flow communication via first conduit section 120. Particulate filter 126 is in flow communication with air source 116 and confined space 108, and facilitates removing particulates entrained in air received at particulate filter 126 such that a flow of filtered air 130 is discharged therefrom. Anti-microbial filter 128 is positioned downstream from particulate filter 126, and receives the flow of filtered air 130 channeled through first conduit section 120. As will be described in more detail below, anti-microbial filter 128 facilitates lysing microorganisms entrained in the flow of filtered air 130 such that a flow of purified air 132 is discharged therefrom. The flow of purified air 132 is provided to confined space 108 via second conduit section 122, and a recirculation duct 134 provides flow communication between confined space 108 and particulate filter 126. Accordingly, a flow of recirculated air 136 discharged from confined space 108 may be channeled through recirculation duct 134 and mixed with ambient air 124 for further circulation within air supply system 114.

Figure 3:
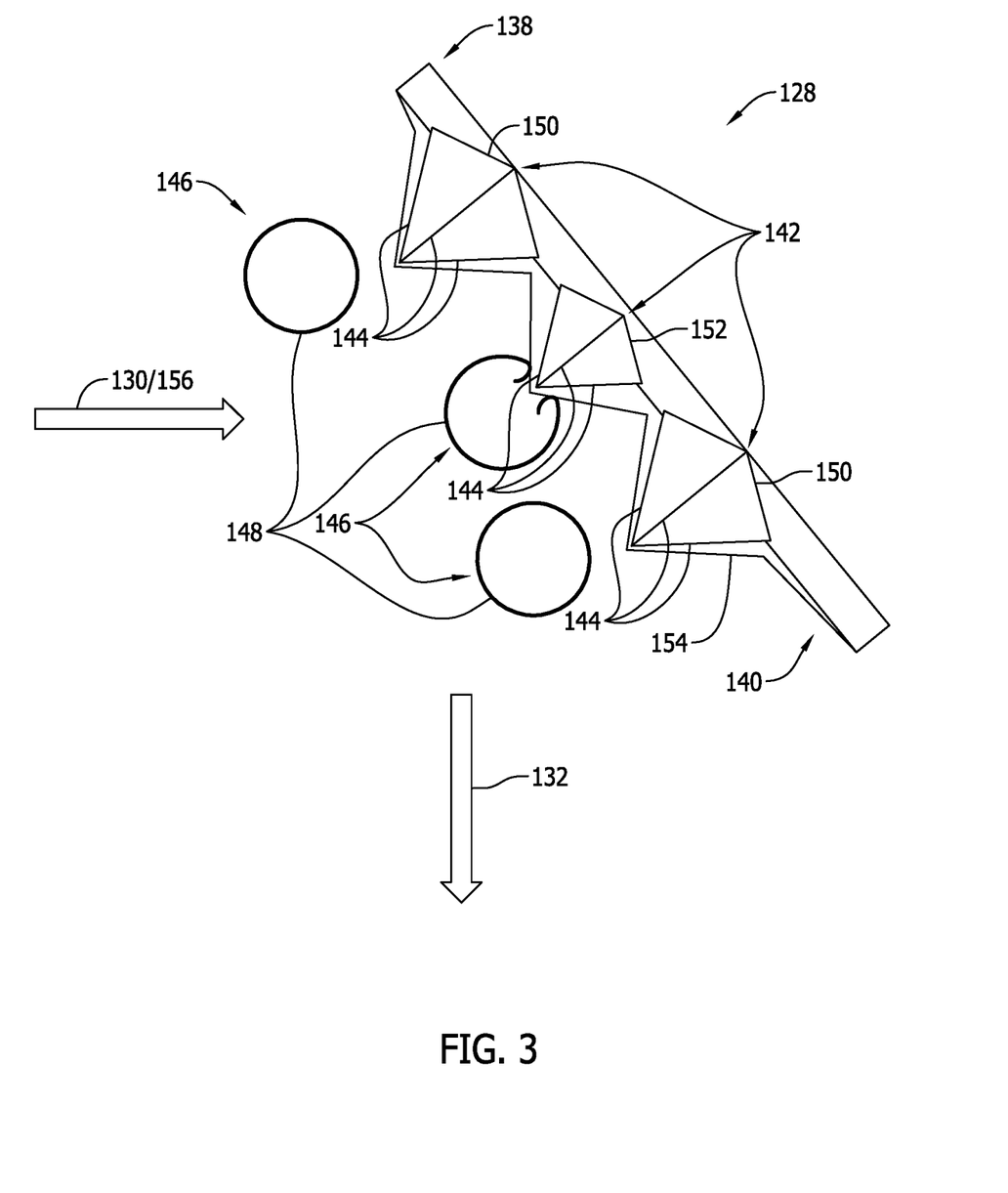

FIG. 3 is a partial view illustration of an example anti-microbial filter 128 that may be used in air supply system 114 (shown in FIG. 2). In the example implementation, anti-microbial filter 128 is formed from at least one substrate 138 having a filtration surface 140 and a plurality of atomically sharp surface features 142 formed on filtration surface 140. Each surface feature 142 includes at least one atomically sharp edge 144 that provides a point of impact for microorganisms 146 entrained in the flow of filtered air 130. As will be explained in more detail below, causing microorganisms 146 to contact surface features 142 with a force greater than a threshold level facilitates lysing a membrane 148 of microorganisms 146, thereby resulting in its eventual destruction.

As used herein, "atomically sharp" refers to an edge, grain, or crystal boundary that ends in a single atom of a subject material, or an edge/crystal boundary with a nanometer or sub-nanometer order of dimension as defined by one or more atoms. The subject material may include, but is not limited to, mono-crystalline silicon, graphene, and noble metals such as ruthenium, rhodium, palladium, silver, osmium, iridium, platinum, and gold. The size of the edge/crystal boundary may be determined using scanning profilometers, atomic force microscopy, and/or scanning electron microscopy.

The use of mono-crystalline silicon to form surface features 142 is advantageous because of its ability to form an atomically sharp tip and atomically sharp side edges, and because it has an ultimate tensile strength (i.e., about 500 MPa) substantially equivalent to stainless steel. The use of mono-crystalline silicon facilitates producing durable, repeatable, and resilient surface features 142.

Substrate 138 may be formed from any material that enables anti-microbial filter 128 to function as described herein. An example substrate material includes, but is not limited to, mono-crystalline silicon. In one implementation, atomically sharp surface features 142 are formed as a result of anisotropic etching of the substrate material to produce a micro-machined spike field on filtration surface 140. For example, a masking material (e.g., metals, nitrides, oxides, and positive and negative photoresists) may be applied to the substrate material in a predetermined pattern, and portions of the substrate material may be removed from around the masking material. Accordingly, anti-microbial filter 128 may be fabricated from multiple etched substrates 138 arranged in an array, or may be fabricated from a single substrate 138 having a surface area approximately equal to that of the array.

The surface features 142 resulting from the anisotropic etching of substrate 138 are illustrated as having a pyramidal shape. However, the anisotropic etching may be performed to define surface features 142 having any suitable shape, geometric or otherwise, having at least one atomically sharp edge 144. In an alternative implementation, surface features 142 are grown on substrate 138, such as in an epitaxial growth process. The epitaxial growth process is defined as the condensation of gas precursors to form a film on a substrate. Liquid precursors are also used, although the vapor phase from molecular beams is more commonly used. Vapor precursors are obtained by Chemical Vapor Deposition (CVD) and laser ablation. It is also possible to anodically bond materials together. Anodic bonding is a wafer bonding process to seal glass to either silicon or metal without introducing an intermediate layer, and is commonly used to seal glass to silicon wafers in electronics and microfluidics.

Surface features 142 can have any size that enables anti-microbial filter 128 to function as described herein. For example, surface features 142 may have an average pyramid size of less than about 50 microns, less than about 25 microns, less than about 15 microns, less than about 10 microns, less than about 5 microns, or less than about 2.5 microns in both the width and height dimensions relative to filtration surface 140. In addition, in the example implementation, the plurality of atomically sharp surface features 142 includes first atomically sharp surface features 150 and second atomically sharp surface features 152 that differ from each other by at least one physical characteristic (e.g., shape or size). Accordingly, a turbulent and non-uniform array of surface features 142 is defined on filtration surface 140 to facilitate enhancing lysis of microorganisms 146 by creating a surface with randomly shaped and positioned surface features. Alternatively, surface features 142 of uniform shape and size are defined on filtration surface 140, and/or filtration surface 140 is defined by regions including non-uniform surface features 142, and regions including uniform surface features 142.

In the example implementation, a layer 154 of coating material extends across filtration surface 140 and the plurality of atomically sharp surface features 142. Any coating material may be used that enables anti-microbial filter 128 to function as described herein. In one implementation, the coating material is selected to enhance the durability of surface features 142, and may be fabricated from a crystalline material such as diamond or sapphire. Alternatively, or additionally, layer 154 is formed from an electrically conductive material (e.g., noble metals). The electrically conductive material may have a greater electrical conductivity than the material of substrate 138 such that the electrical conductivity of anti-microbial filter 128 is enhanced. Layer 154 may be distributed across substantially the entire surface area of filtration surface 140 to facilitate providing uniform conductivity across filtration surface 140. Accordingly, as will be described in more detail below, enhancing the electrical conductivity of filtration surface 140 enables anti-microbial filter 128 to more efficiently lyse microorganisms 146. In alternative implementations, the coating material may be an anti-microbial material such as copper, silver, and alloys thereof.

Figure 4:
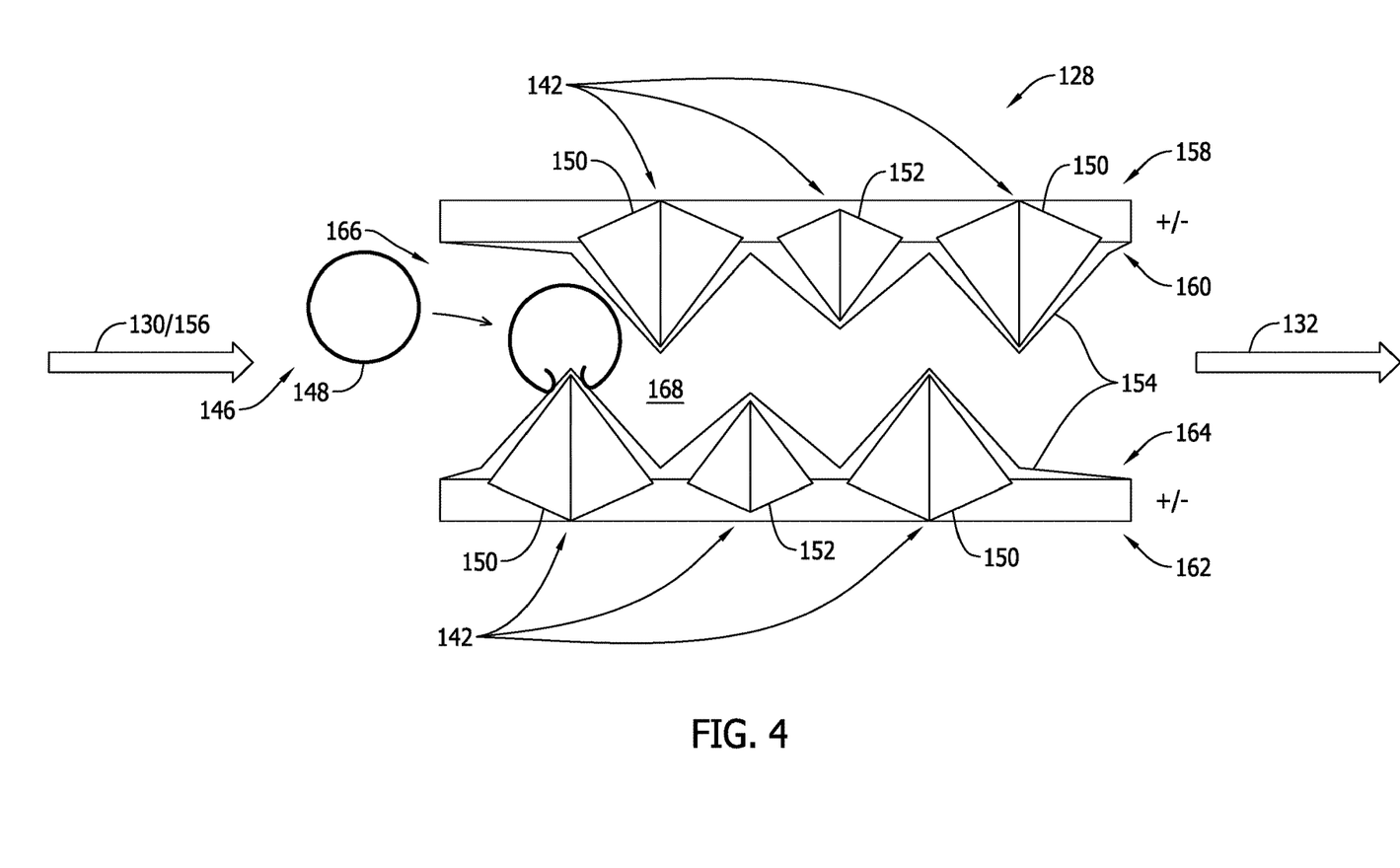
Figure 5:
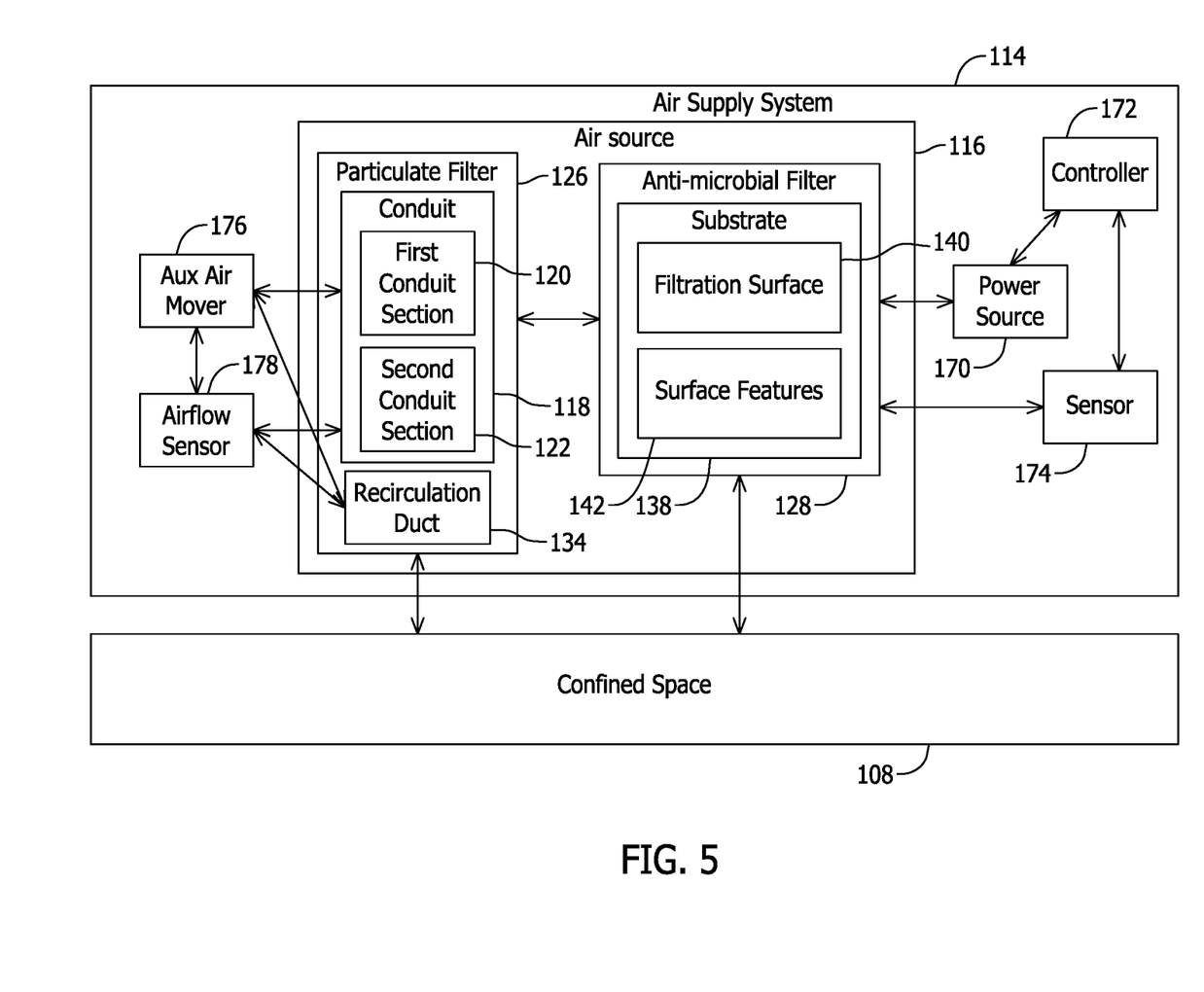

As shown in FIG. 3, the flow of filtered air 130 is channeled through first conduit section 120, and filtration surface 140 is oriented to initiate contact between microorganisms 146 and surface features 142. For example, filtration surface 140 may be oriented obliquely or perpendicularly relative an airflow direction 156 of the flow of filtered air 130. The airflow deflected from filtration surface 140 forms the flow of purified air 132. As described above, the flow of purified air 132 may be recirculated towards anti-microbial filter 128, as a part of the flow of recirculated air 136, after passing through confined space 108 (shown in FIG. 2) to further enhance lysing of microorganisms 146 entrained therein.

FIG. 4 is a partial view illustration of an alternative anti-microbial filter 128 that may be used in air supply system 114 (shown in FIG. 2). In the example implementation, anti-microbial filter 128 includes a first substrate 158 having a first filtration surface 160, and a second substrate 162 having a second filtration surface 164. First filtration surface 160 and second filtration surface 164 are spaced from each other to define an airflow path 166 therebetween, and at least a portion of the flow of filtered air 130 is routed through airflow path 166. The spacing between first filtration surface 160 and second filtration surface 164 is based at least partially on the size of microorganisms 146, which can be defined within a range between about 20 nanometers to about 400 nanometers.

The spacing is selected to facilitate initiating contact between microorganisms 146 and surface features 142 on at least one of first filtration surface 160 or second filtration surface 164. For example, in one implementation, a gap 168 defined between adjacent surface features 142 on first filtration surface 160 and second filtration surface 164 may be smaller than an average size of microorganisms 146 entrained in the flow of filtered air 130. Accordingly, contact is initiated between microorganisms 146 and surface features 142 as microorganisms 146 are forced through airflow path 166. In an alternative implementation, gap 168 may be larger than the average size of microorganisms 146, and contact is facilitated to be initiated via electrical biasing of anti-microbial filter 128, as will be explained in more detail below. To ensure a sufficient amount of purified air 132 is received in confined space 108, multiple substrate 158 and 162 pairs may be arranged in a stacked array to increase the flow through capacity of anti-microbial filter 128. For example, by virtue of the size of gap 168, each pair has a limited flow through capacity for channeling airflow therethrough. Accordingly, multiple substrate pairs can be arranged to receive and discharge airflow to satisfy airflow needs of confined space 108, for example.

Referring again to FIG. 2, air supply system 114 includes a power source 170 electrically coupled with anti-microbial filter 128, a controller 172 in communication with power source 170, and a sensor 174 coupled to anti-microbial filter 128. Sensor 174 is also in communication with controller 172. Operation of power source 170 is controlled by controller 172, and controller 172 can control operation of power source 170 based on feedback received from sensor 174.

In one implementation, power source 170 provides a voltage to anti-microbial filter 128 to facilitate lysing microorganisms 146 entrained in the flow of filtered air 130. For example, in operation, power source 170 electrically biases anti-microbial filter 128 with a positive charge or a negative charge. As shown in FIG. 3, filtration surface 140 can be either positively charged or negatively charged and, as shown in FIG. 4, first filtration surface 160 may be positively charged and second filtration surface 164 negatively charged, or vice versa. Particles such as microorganisms 146 inherently carry a residual surface charge. As such, electrically biasing anti-microbial filter 128 facilitates attracting microorganisms 146 to anti-microbial filter 128 to enhance the lysis thereof. Alternatively or additionally, power source 170 may provide an electrical discharge from anti-microbial filter 128. The electrical discharge is for lysing at least some of microorganisms 146 entrained in the flow of filtered air 130, such as those that are in close proximity to, but that may not come into contact with, filtration surface 140.

In one implementation, sensor 174 monitors a capacitance across anti-microbial filter 128. Monitoring the capacitance and/or changes in the capacitance facilitates providing an indication of a potential buildup of contamination on the electrically conductive filtration surface 140. When the capacitance and/or the change in capacitance reaches or exceeds a threshold level, controller 172 causes power source 170 to provide a surge charge to anti-microbial filter 128. The surge charge is for removing contamination from anti-microbial filter 128. Accordingly, power source 170 facilitates periodically cleaning anti-microbial filter 128.

The movement of airflow channeled through conduit 118 and recirculation duct 134 can be effectuated by one or more air moving devices (not shown), such as a pump, a fan, or the like. The one or more air moving devices may accelerate the airflow to a first velocity, for example. In the example implementation, air supply system 114 also includes an auxiliary air mover 176 and an airflow sensor 178 in communication with each other, and also both in flow communication with first conduit section 120. Auxiliary air mover 176 can be a pump, a fan, or the like. Airflow sensor 178 monitors the airflow velocity of the flow of filtered air 130 channeled through first conduit section 120, and provides airflow velocity data to auxiliary air mover 176. Auxiliary air mover 176 is selectively operable to facilitate accelerating the flow of filtered air 130 from the first velocity to a greater second velocity. As described above, anti-microbial filter 128 facilitates purifying filtered air 130 by mechanically damaging or lysing microorganisms 146 (shown in FIGS. 3 and 4) entrained therein by causing microorganisms 146 to impact atomically sharp surface features 142 (shown in FIGS. 3 and 4). In general, microorganisms 146 must contact surface features 142 with a predetermined amount of force to facilitate piercing and/or damaging membrane 148 (shown in FIGS. 3 and 4) with atomically sharp edge 144 (shown in FIGS. 3 and 4). In one implementation, the mass or average mass of microorganisms 146 entrained in filtered air 130 may be a known or estimatable value. Accordingly, based on the mass of microorganisms 146, auxiliary air mover 176 facilitates selectively accelerating the flow of filtered air 130 to the second velocity to cause microorganisms 146 to contact surface features 142 with sufficient lysing force.

This written description uses examples to disclose various implementations, including the best mode, and also to enable any person skilled in the art to practice the various implementations, including making and using any devices or systems and performing any incorporated methods. The patentable scope of the disclosure is defined by the claims, and may include other examples that occur to those skilled in the art after reading this specification. Such other examples are intended to be within the scope of the claims if they have structural elements that do not differ from the literal language of the claims, or if they include equivalent structural elements with insubstantial differences from the literal language of the claims.

What is claimed is:

1. An air supply system comprising:
   a conduit for channeling a flow of air therethrough, wherein the flow of air has microorganisms entrained therein;
   an anti-microbial filter in flow communication with the flow of air, wherein the anti-microbial filter comprises:
   a first air-impermeable substrate having a first filtration surface and a second air-impermeable substrate having a second filtration surface and spaced from each other between about 20 nanometers to about 400 nanometers, each of the first and second filtration surfaces having a plurality of atomically sharp surface features for non-selective lysing of at least some of the microorganisms that contact the anti- microbial filter, wherein the first and second filtration surfaces are oriented obliquely relative to an airflow direction of the flow of air; and
   a sensor operable to monitor a capacitance across the anti-microbial filter;
   a power source electrically connected to the anti-microbial filter; and
   a controller in communication with the power source, wherein the controller causes the power source to provide a surge charge to remove contamination from the anti-microbial filter when the capacitance measured by the sensor reaches a threshold value.

2. The air supply system in accordance with claim 1 further comprising a layer of coating material on each of the pluralities of atomically sharp surface features, wherein the coating material enhances at least one of the durability or the conductivity of the plurality of atomically sharp surface features.

3. The air supply system in accordance with claim 1, wherein the controller causes the power source to at least one of:
   electrically bias the anti-microbial filter with a positive charge or a negative charge to attract the microorganisms to the anti-microbial filter; or
   provide an electrical discharge from the anti-microbial filter, wherein the electrical discharge lyses at least some of the microorganisms entrained in the flow of air.

4. The air supply system in accordance with claim 1, wherein each of the pluralities of atomically sharp surface features comprises first atomically sharp surface features and second atomically sharp surface features that differ from each other by at least one physical characteristic.

5. The air supply system of claim 1, wherein the system is adapted to:
   channel a flow of air, having microorganisms entrained therein, towards the anti-microbial filter,
   control a velocity of the flow of air, wherein the velocity is selected to facilitate non-selective lysing of at least some of the microorganisms that contact the anti-microbial filter; and
   discharge a flow of purified air from the anti-microbial filter.

6. The system in accordance with claim 5 wherein the system is adapted to provide a voltage to the anti-microbial filter.

7. The system in accordance with claim 6 wherein the system is adapted to remove particulates entrained in the flow of air upstream from the anti-microbial filter.

8. The system in accordance with claim 7 wherein the system is adapted to channel a flow of recirculated air, formed from the flow of purified air, towards the anti-microbial filter such that microorganisms within the flow of purified air discharged from anti-microbial filter are recirculated towards the anti-microbial filter.

9. The system in accordance with claim 8, wherein the system is adapted to control a velocity of the flow of air by selectively accelerating the flow of air towards the anti-microbial filter at a velocity greater than a predetermined threshold.

10. An air supply system comprising:
    a conduit for channeling a flow of air therethrough, wherein the flow of air has microorganisms entrained therein;
    an anti-microbial filter in flow communication with the flow of air, wherein the anti-microbial filter comprises a first air-impermeable substrate having a first filtration surface and a second air-impermeable substrate having a second filtration surface and spaced from each other between about 20 nanometers to about 400 nanometers to define an airflow path therebetween, each of the first and second filtration surfaces comprising a plurality of atomically sharp surface features for non-selective lysing of at least some of the microorganisms that contact the anti-microbial filter;
    a power source electrically connected to the anti-microbial filter; and
    a controller in communication with the power source, wherein the controller causes the power source to provide a surge charge to remove contamination from the anti-microbial filter when a measured capacitance reaches a threshold value.

11. The air supply system in accordance with claim 10, wherein each atomically sharp surface feature comprises at least one atomically sharp edge, the first and second filtration surfaces oriented such that the at least one atomically sharp edge is oriented obliquely or perpendicularly relative to an airflow direction of the flow of air.

12. An aircraft comprising:
    a confined space;
    the air supply system of claim 10; and
    a filter upstream from the anti-microbial filter, wherein the filter removes particulates entrained in the flow of air.

13. The aircraft in accordance with claim 12 further comprising:

an auxiliary air mover that selectively accelerates the flow of air towards the anti-microbial filter at a velocity greater than a predetermined threshold; and an airflow sensor in communication with the auxiliary air mover, wherein the auxiliary air mover selectively accelerates the flow of air based on airflow velocity data received from the airflow sensor.

14. The aircraft in accordance with claim 12 further comprising a recirculation duct provides a flow of recirculated air from the confined space to the air supply system such that microorganisms within the flow of purified air discharged from anti-microbial filter are recirculated towards the anti-microbial filter.

15. The aircraft in accordance with claim 12 further comprising a layer of coating material on the each of the pluralities of atomically sharp surface features, wherein the coating material enhances at least one of the durability or the conductivity of the plurality of atomically sharp surface features.

16. The aircraft in accordance with claim 12, wherein the controller causes the power source to at least one of:

electrically bias the anti-microbial filter with a positive charge or a negative charge to attract the microorganisms to the anti-microbial filter; or provide an electrical discharge from the anti-microbial filter, wherein the electrical discharge is for lysing at least some of the microorganisms entrained in the flow of air.

17. An air supply system comprising:

a conduit for channeling a flow of air therethrough, wherein the flow of air has microorganisms entrained therein;

an anti-microbial filter in flow communication with the flow of air, wherein the anti-microbial filter comprises a first air-impermeable substrate having a first filtration surface and a second air-impermeable substrate having a second filtration surface and spaced from each other between about 20 nanometers and about 400 nanometers, each of the first and second filtration surfaces having a plurality of atomically sharp surface features for non-selective lysing of at least some of the microorganisms that contact the anti-microbial filter, wherein the filtration surface is oriented obliquely relative to an airflow direction of the flow of air; and a power source electrically connected to the anti-microbial filter, wherein the power source is operable to provide a surge charge to clean the anti-microbial filter.

18. The air supply system in accordance with claim 17, wherein each atomically sharp surface feature comprises at least one atomically sharp edge, the first and second filtration surfaces oriented such that the at least one atomically sharp edge is oriented obliquely or perpendicularly relative to an airflow direction of the flow of air.

19. The air supply system in accordance with claim 17, further comprising a layer of coating material on each of the pluralities of atomically sharp surface features, wherein the coating material enhances at least one of the durability or the conductivity of the plurality of atomically sharp surface features.

20. The air supply system in accordance with claim 17, wherein each of the pluralities of atomically sharp surface features comprises first atomically sharp surface features and second atomically sharp surface features that differ from each other by at least one physical characteristic.

* * * * *